(12) United States Patent
Magee

(10) Patent No.: US 7,377,151 B1
(45) Date of Patent: May 27, 2008

(54) FUEL TESTER

(76) Inventor: Bryan Magee, 1102 S. Franklin Rd., Indianapolis, IN (US) 46239

( * ) Notice: Subject to any disclaimer, the term of this patent is extended or adjusted under 35 U.S.C. 154(b) by 0 days.

(21) Appl. No.: 11/122,715

(22) Filed: May 5, 2005

(51) Int. Cl.
*G01N 33/22* (2006.01)
(52) U.S. Cl. .................................. 73/61.61
(58) Field of Classification Search ............... 73/61.61
See application file for complete search history.

(56) References Cited

U.S. PATENT DOCUMENTS

| | | | | |
|---|---|---|---|---|
| 3,576,989 | A | * | 5/1971 | Schwartz .................... 362/135 |
| 3,976,572 | A | | 8/1976 | Reick |
| 3,987,294 | A | * | 10/1976 | Carlson ...................... 362/101 |
| 4,289,027 | A | | 9/1981 | Gleaves et al. |
| 4,700,580 | A | | 10/1987 | Kamin |
| 4,804,273 | A | * | 2/1989 | Tondello et al. ............ 356/427 |
| 4,967,595 | A | | 11/1990 | Olson |
| 5,180,221 | A | * | 1/1993 | Yoder ......................... 362/101 |
| 7,134,932 | B1 | * | 11/2006 | Carrasco et al. ............ 446/227 |
| 2003/0058450 | A1 | * | 3/2003 | Mosley et al. .............. 356/436 |
| 2003/0081408 | A1 | * | 5/2003 | Tai .............................. 362/101 |
| 2004/0042201 | A1 | * | 3/2004 | Lee ............................. 362/101 |

* cited by examiner

*Primary Examiner*—Hezron Williams
*Assistant Examiner*—Paul M West
(74) *Attorney, Agent, or Firm*—Woodard, Emhardt, Moriarty, McNett & Henry LLP

(57) ABSTRACT

A fuel tester is provided, which may be used to test for the presence of a contaminant such as water in a sample of fuel. In one embodiment, the fuel tester is a tube with a receiving end configured to attach to a sample container. The sample container holds a sample of fuel obtained from a device such as an aircraft. The fuel tester also includes a light source, e.g. a light emitting diode that is positioned in the tube to emit light on the sample of fuel in the sample container. If water is present in the sample of fuel, the water will form a separate layer from the fuel. The water layer will appear as a lighter shade of color and the fuel layer will appear as a darker shade of color on visual inspection by a user. The non-uniformity in color of the sample will alert the user that water is present in the fuel sample.

16 Claims, 3 Drawing Sheets

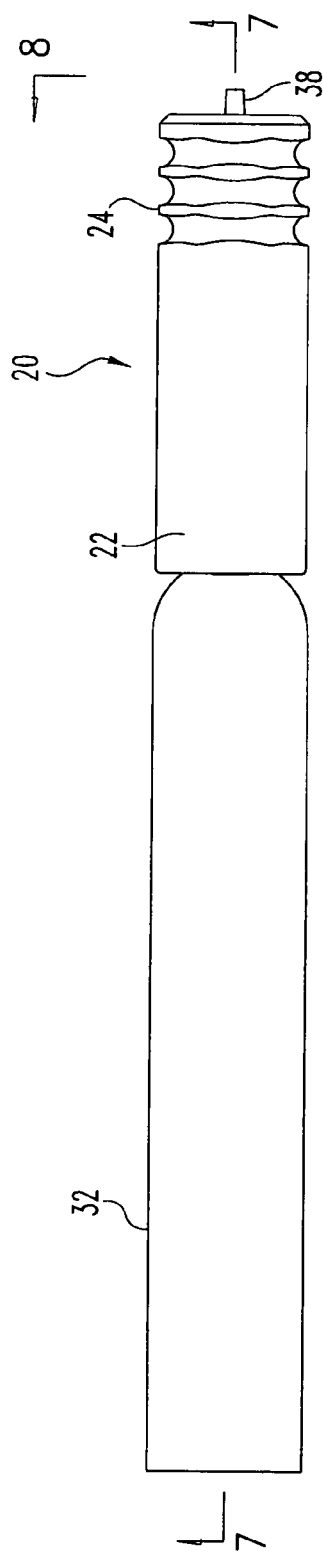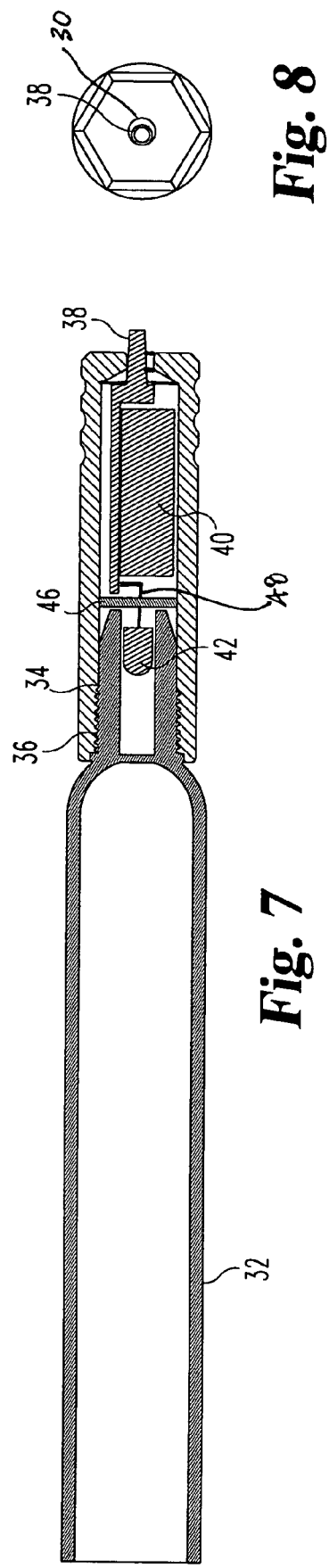

ated embodiment.

FUEL TESTER

BACKGROUND

For the maintenance of fueled devices such as aircraft, and the safety of passengers and flight crew, it is known to periodically test for the presence of contaminants in a fuel line. One such contaminant is water that may have entered the fuel line and contaminated the fuel.

Often aircraft have a quick-release or other type of valve, positioned on the underside of one or both wings or on another location of the aircraft, from which a sample of fuel from the fuel tank or fuel line may be collected. A fuel sample may be collected in a vessel, such as a clear plastic body, and then tested for the presence of contaminants such as water. One form of testing includes using a float with a density greater than fuel but less than water. The float is placed in a collection vessel and a sample of fuel is collected in the vessel. If there is water present in the fuel, the water will form a separate phase or layer at the bottom of the vessel. The fuel will form a layer above the water in the vessel. The float will sit at the interface between the water and fuel thereby indicating to the user that water is present in the fuel sample, and thus the fuel line or tank may be contaminated.

Another form of testing for the presence of contaminants in a sample of fuel uses a filter element. The filter element typically is positioned in a vessel, such as a clear cylinder, thereby dividing the vessel into an upper chamber and a lower chamber. A sample of fuel is collected in the upper chamber. The filter element may be formed of a selectively-permeable material which blocks the flow of one or more contaminants, e.g. a hydrophobic material that blocks water, and is permeable only to fuel. In that example, the fuel will pass through the filter element into the lower chamber and any contaminant present in the sample will remain in the upper chamber thereby visually alerting the user to the presence of the contaminant.

Testing for the presence of contaminants such as water in a fuel sample can be time consuming. Further, convenient testing or inspection of fuel samples should be available immediately on taking the sample, regardless of the surrounding conditions. While instruments have been developed to detect water in a fuel sample, there remains a need to determine quickly and accurately whether such contaminants are present in a fuel sample in any environment.

BRIEF DESCRIPTION OF THE DRAWINGS

FIG. 6 is a top view of an embodiment of a sample container attached to the embodiment shown in FIG. 1.

FIG. 7 is a cross-sectional view taken along the lines 7-7 in FIG. 6 showing the embodiment of FIG. 6.

FIG. 8 is a side view taken along the lines 8-8 in FIG. 6 and viewed in the direction of the arrows.

DESCRIPTION OF THE ILLUSTRATED EMBODIMENT

Figure 1:
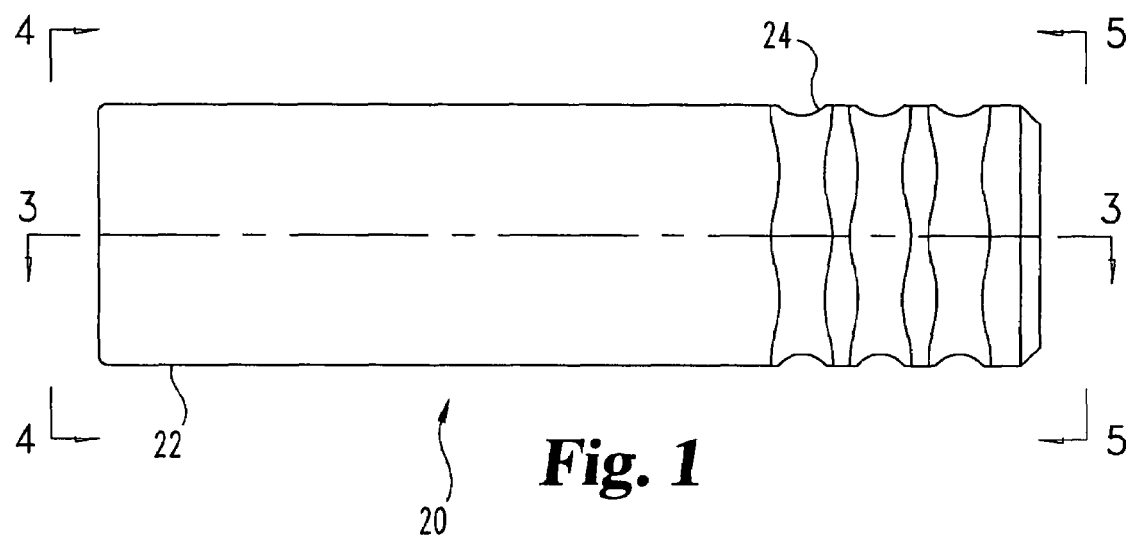
FIG. 1 is a top view of an embodiment of a fuel tester.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Figure 2:
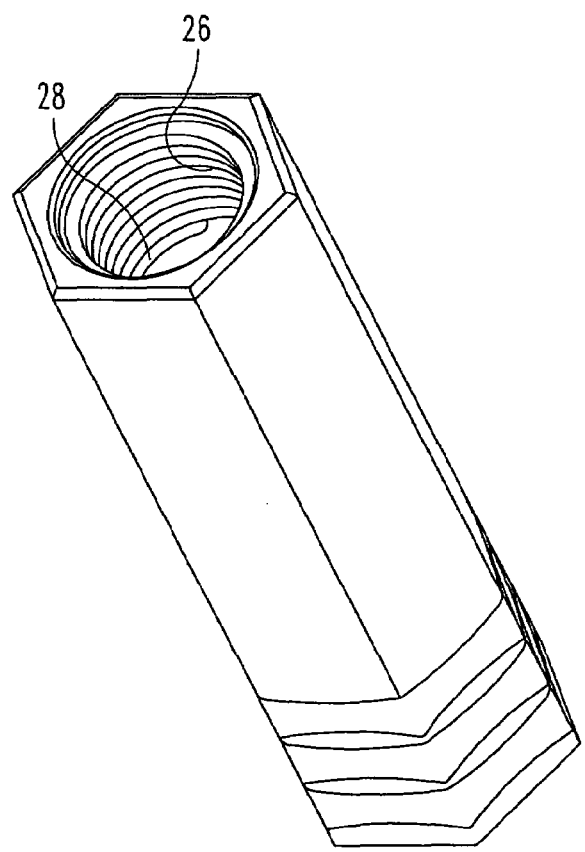
FIG. 2 is a perspective view of the embodiment of FIG. 1.
Figure 3:
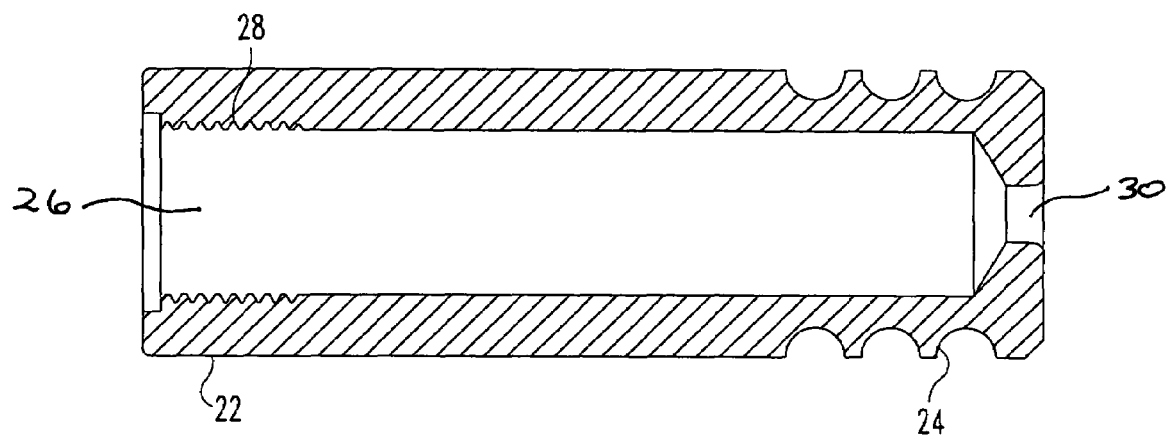
FIG. 3 is a cross-sectional view taken along the lines 3-3 in FIG. 1 showing the embodiment of FIG. 1.

Looking first at FIGS. 1-3, there is shown an embodiment of an aircraft fuel tester 20. Aircraft fuel tester 20 may be made for testing for the presence of a contaminant in a fuel sample. The description below focuses on water as the contaminant to be tested for, but it will be recognized that the illustrated embodiment and other embodiments can be used to test for other contaminants as well.

Fuel tester 20, in the embodiment shown in FIG. 1, includes a receiving end 22, a handle end 24, and a passageway 26. In the illustrated embodiment, fuel tester 20 is an elongated tubular piece. In this embodiment, the length of fuel tester 20 is approximately 3 inches. Fuel tester 20 may have a hexagonal cross sectional shape as shown in FIG. 2 or may be of other appropriate cross sectional shape. In one embodiment, the fuel tester 20 may have ridges on the handle end 24. As should be appreciated, ridges may assist a user in grasping or holding the fuel tester 20. The ridges may be formed from a radius of approximately 0.1 inches and spaced approximately 0.25 inches apart. In another embodiment, the fuel tester 20 may have a smooth surface on the handle end 24. In one embodiment, fuel tester 20 may be formed of transparent material such as plastic or glass. In another embodiment, fuel tester 20 may be formed of an opaque material.

Figure 4:
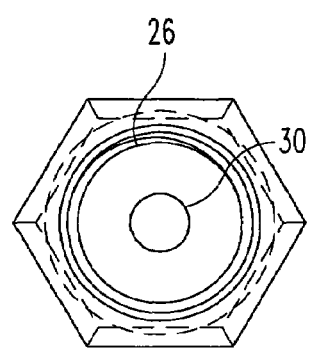
FIG. 4 is a side view taken along the lines 4-4 in FIG. 1 and viewed in the direction of the arrows.
Figure 5:
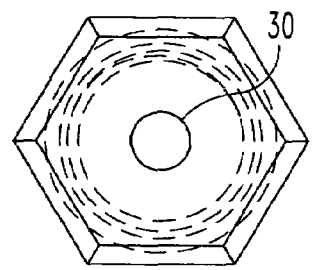
FIG. 5 is a side view taken along the lines 5-5 in FIG. 1 and viewed in the direction of the arrows.

Passageway 26 may have a circular cross sectional shape or may be of other appropriate cross sectional shape. In one embodiment, passageway 26 is a circular cross sectional shape with approximately 0.5 inches diameter. As shown in FIGS. 2 and 3, passageway 26 may include an engagement portion 28 for engaging a sample container or a testing tube, as described below. In this embodiment, engagement portion 28 may include a plurality of threads. Further, the length of the engagement portion 28 is approximately 0.5 inches with 0.625 inches—18 NF threads. In another embodiment, engagement portion 28 may include a smooth surface or may have another form of attachment, e.g. detents, snap-fit, bayonet connection, or others, to attach the fuel tester 20 to a sample container. Passageway 26 includes an aperture 30 at the handle end 24 of the fuel tester 20 as shown in FIGS. 3 and 4. Passageway 26 extends the length of the fuel tester 20 and tapers at the handle end 24 to form aperture 30. In the embodiments shown in FIGS. 4 and 5, aperture 30 is a circular shape; however, aperture 30 may be of other cross sectional shape. In one embodiment, aperture 30 is a circular shape with a diameter of approximately 0.2 inches. As described below, aperture 30 may be sized to receive a momentary switch or some other on-off button.

In one embodiment shown in FIG. 6, a testing tube or sample container 32 is attached to the fuel tester 20. The sample container 32 is sized to hold a sample of fuel. The sample container 32 includes a projection end 34 configured to attach to the receiving end 22 of the fuel tester 20. In the illustrated embodiment, the projection end 34 is a circular tube sized to fit in passageway 26. Further, the projection end 34 is sized and configured to receive a light bulb, as described below. In this embodiment, the projection end 34 is configured such that a light bulb illuminates the sample of fuel through the projection end 34. In another embodiment, the projection end 34 is configured such that a light bulb illuminates the sample of fuel through another portion of the sample container 32. The projection end 34 includes threads 36 to threadably engage with and attach to the engagement portion 28 of the receiving end 22. In another embodiment, the projection end 34 may be configured differently to attach to the receiving end 22. Sample container 32 may be formed of clear or transparent material that allows a user to visually inspect the fuel sample contained therein. In another embodiment, the sample container 32 may include wrenching flats, a screwdriver head or other tool or structure useful for opening drain valves of aircraft. Fuel drained through the drain valve is caught, collected, and held by the sample container 32.

In one embodiment, fuel tester 20 further includes a switch 38 that may be a momentary switch (e.g. a switch that is biased to the "off" position and must be continuously pressed to complete a circuit), a battery 40, and a light bulb 42. Switch 38 is sized to extend through aperture 30 such that a user may press or otherwise engage switch 38. Switch 38 is connected to battery 40 and light bulb 42. In the illustrated embodiment, switch 38 is a spring-loaded contact that, when pressed, connects contacts to complete a circuit between battery 40 and light bulb 42. When pressure is removed from switch 38, the spring biases switch 38 away from such contacts, disconnecting them and breaking the circuit.

In the embodiment illustrated in FIG. 7, battery 40 is sized to fit in passageway 26. In one embodiment, battery 40 provides approximately twelve volts. In another embodiment, battery 40 may have another appropriate voltage. In yet another embodiment, battery 40 may comprise a plurality of batteries. Any size of battery, such as AAA-size or watch-type batteries, that will energize bulb 42 may be used. Smaller batteries will reduce the overall size of embodiments of tester 20.

As shown in FIG. 7, light bulb 42 is sized to fit in passageway 26. In particular, light bulb 42 is sized to fit in the projection end 34 of the sample container 32. Light bulb 42 is positioned in the passageway 26 to illuminate a fuel sample contained in sample container 32. In particular, light bulb 42 may be used to check for the presence of water in a sample of fuel in the sample container 32. In one embodiment, light bulb 42 is a blue light emitting diode (LED) that emits 10,000 millicandela. The term "light bulb" or "bulb" is thus not intended to indicate only incandescent lighting. Further, sources that emit other colors of light, such as red, white or green, may be used. Light bulb 42 illuminates the contents of sample container 32, and water (for example) appears as a lighter or paler shade of blue (in the embodiment in which a blue light source is used) than the fuel. A fuel sample contaminated by water will appear to the user to have a disconnect in the liquid sample such that water will appear as a light blue layer and fuel will appear as a dark blue layer when the light bulb 42 emits blue light. In this way, a fuel sample may be checked for the presence of a contaminant, such as water, in a relatively poorly lighted or dark environment.

In the illustrated embodiment, fuel tester 20 includes a seal 46 as shown in FIG. 7. Seal 46 is sized to fit in passageway 26 and positioned between battery 40 and light bulb 42 in passageway 26. In this embodiment, seal 46 is a circular shape, and may have a diameter of approximately 0.5 inches. Seal 46 is configured such that connectors 48 between battery 40 and light bulb 42 pass through seal 46. Seal 46 may be formed from rubber or other resilient materials, or may be made of other appropriate substance.

In use, a user connects a sample container 32 to the fuel tester 20 by inserting the projection end 34 of the sample container 32 into the receiving end 22 of the fuel tester 20. The user threadably connects threads 36 to engagement portion 28. A fuel sample from an aircraft is collected in the sample chamber 32. In a particular embodiment, a cap or other cover may be placed on the open end of the sample chamber 32 to protect or substantially enclose the fuel sample. A user may push or press switch 38 to complete a circuit from battery 40 to light bulb 42. The light bulb 42 emits light, e.g. blue light, onto the fuel sample. The user visually inspects the fuel sample to determine if water is present in the fuel. In particular, the user looks for variations in the coloration within the lighted fuel sample. Water will show as a light shade of blue within sample chamber 32 and below a darker shade of blue, the darker shade of blue representing fuel. Seeing separate layers in sample chamber 32 having somewhat different colorations alerts the user that water is present in the fuel sample and likely in the fuel line or tank from which the fuel sample was taken.

It will be seen that other contaminants can also be tested for using the illustrated embodiment or other embodiments. Other contaminants having densities different from fuel, and that will show a different color under illumination from that of the fuel, can be tested for.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Various types or colors of light sources, various types of batteries, switches or other circuit components can be used. Multiple light sources, batteries, switches, and/or circuit components can be included. While the illustrated embodiment of sample chamber 32 is of transparent plastic, other materials can be used. As examples, glass or translucent plastics could also be used.

Further, although the illustrated embodiment is described as being particularly useful in testing fuel from aircraft, it will be understood that it or other embodiments could be used for testing fuel in other machines or modes of transportation. For example, any device using a hydrocarbon-based fuel, such as an automobile or a small engine (such as for a lawn mower), may accumulate water or other contaminants in a fuel tank or line. Fuel samples from such devices can be tested for contamination largely as previously described.

What is claimed is:

1. A method for testing for a contaminant a sample of fuel comprising:
    providing a fuel tester having a receptacle connected to a sample container, said receptacle connected to a light source, a battery and a switch electrically connected together;
    collecting a sample of fuel in said sample container;
    emitting light from said light source on the sample in said sample container; and
    visually inspecting the sample for color variation therein wherein said fuel tester is hand-held and portable, and said collecting step includes allowing said sample to exit a vehicle and enter said sample container.

2. A method according to claim 1, wherein said light source is a light emitting diode.

3. A method according to claim 1, wherein the contaminant tested for is water, and the color variation is such that a fuel layer appears a darker shade of a color and a water layer appears a lighter shade of a color.

4. The method of claim 1, wherein said emitting includes pressing said switch.

5. The method of claim 4, wherein said fuel tester has an exterior surface from which said switch at least partially protrudes, and said pressing includes moving a portion of said switch toward said exterior surface.

6. The method of claim 5, wherein said exterior surface is an end surface facing generally away from said sample container.

7. The method of claim 1, wherein said emitting include pressing and holding said switch.

8. The method of claim 1, wherein said switch is spring-loaded and biased to a disconnected state.

9. The method of claim 1, wherein said sample is of aviation fuel, and said light source emits blue light.

10. The method of claim 1, wherein said sample is of jet fuel, and said light source emits white light.

11. The method of claim 1, wherein said sample container has an open end, and further comprising the step of covering said open end.

12. The method of claim 1, wherein said vehicle from which said sample is collected is an aircraft.

13. The method of claim 1, wherein said sample container is transparent.

14. The method of claim 1, wherein said sample container is translucent.

15. The method of claim 1, wherein said sample container is an elongated tube.

16. The method of claim 1, further comprising opening a drain valves of said vehicle using structure included with said sample container.

* * * * *